United States Patent [19]

Loh

[11] 4,045,729
[45] Aug. 30, 1977

[54] GAS DETECTOR

[76] Inventor: Jack C. Loh, 16 Beaufort St., White Plains, N.Y. 10607

[21] Appl. No.: 708,459

[22] Filed: July 26, 1976

[51] Int. Cl.² ........................................... G01N 57/00
[52] U.S. Cl. ............................... 324/71 SN; 73/27 R; 23/254 E; 340/237 R
[58] Field of Search ............... 324/71 SN; 340/237 R; 73/27 R; 23/254 E

[56] References Cited

U.S. PATENT DOCUMENTS

| | | | |
|---|---|---|---|
| 3,695,848 | 10/1972 | Taguchi | 23/254 E |
| 3,751,968 | 8/1973 | Loh et al. | 73/27 R X |
| 3,933,028 | 1/1976 | Laud et al. | 73/27 R X |

Primary Examiner—Rudolph V. Rolinec
Assistant Examiner—Vincent J. Sunderdick
Attorney, Agent, or Firm—Allison C. Collard

[57] ABSTRACT

A gas detector for sensing the presence of a gaseous medium consisting of a helical coil for connection to a dc power source for generating both an electromagnetic field and radiant heat. The coil is wrapped around a tubular sleeve constructed of a sensing material, such as a semiconductor, and disposed in the magnetic and heating fields of the coil. An electrode is disposed in the sleeve so that when a current sensing medium is connected between the electrode and one end of the coil, a current will be produced proportional to the concentration of the gas being detected. In several embodiments, the sleeve is constructed of an n-type semiconductor material, such as zinc oxide, stannic oxide, or gallium oxide and is good for detecting hydrocarbons. If the sleeve is constructed of tungsten trioxide or molybdenum trioxide mixed with silicon dioxide, the sleeve can be used for detecting hydrogen. The sleeve is generally operated at temperatures between 100° and 450° C. An additional battery can be coupled between the current sensing element and one end of the coil for increasing the sensitivity of the sleeve.

8 Claims, 3 Drawing Figures

GAS DETECTOR

This invention relates to a gas detection sensor for the detection of either a specific gas or a group of gases in a given environment.

More specifically, this invention relates to a gas detection apparatus which uses an active solid state sensor with a semiconductor sensing material which is effected by the presence of the gas for detection. The detection of a specific gas or gases is indicated by an increase in electrical current which is induced by an electromagnetic field and flows through the sensing semiconductor or ionic conductor material. The invention utilizes a solid state thermal electromagnetic sensor for gas detection.

Conventional devices utilize catalytic sensors for the detection of a specific gas or vapor in a given atmosphere. Also the prior art gas sensors are passive type devices so that a potential must be applied across the sensing element in order to measure its thermal conductivity or electrical conductivity change. Only two types of gas sensors are generally considered as active sensors. The first of these devices is an electrochemical concentration cell which uses a solid electrolyte of stabilized zirconium oxide as the oxygen sensor. A second type of active device uses electrochemical sensors with a liquid electrolyte. These prior art devices described above have several disadvantages. In the first type of active sensors, the size of the sensor is generally excessively large, its power consumption is high and the reference gas must be supplied to the reference electrode in order to obtain an accurate measurement.

The major problem in using sensors having liquid electrolyte is that the use of the sensors is limited to temperatures below the boiling point of the electrolyte so that the sensor is excluded from any high temperature application.

The present invention overcomes the disadvantages of the above described active devices in providing a solid state thermal electromagnetic sensor as an active device which can be fabricated into a very small size and requires low power consumption during operation. The solid state sensor of the present invention uses a noble metal coil as a heater coil which also generates the electromagnetic field when a DC current is applied to the coil. Disposed within the coil is a sensing material which is a semiconductor or ionic conductor of a type depending upon the gas being detected. The semiconductor or ionic conductor is in the form of a hollow sleeve so that an auxiliary electrode consisting of a wire made from a noble metal such as platinum can be inserted into the semiconductor or ionic conductor sleeve and placed within the path of the induced electrical current. When a DC potential or current is applied across the coil, an electron current flows in the direction from the negative terminal to the positive terminal of the power supply. First of all, there is a temperature increase in the coil, and secondly, there is the creation of an electromagnetic field in the vicinity of the coil. It has been known that many metal oxides can react with certain gas molecules and become catalysts at elevated temperatures. These metal oxides are considered either as semiconductor material (both n-type and p-type) or ionic conducting material.

For example, a material such as zinc oxide which is a typical n-type semi-conductor and reacts with many hydrocarbons as a catalyst at temperatures about 400° C. If the semiconductor material is n-type, then a certain number of free electrons must exist at the elevated temperature. Under the influence of the induced electromagnetic field, these electrons flow inside of the semiconductor in a direction from the south pole, or the end of the coil connected to be the negative terminal, to the north pole or the end connected to the positive terminal of the DC supply. This creates an internal electron current within the semiconductor which can be measured with an ammeter if one terminal of the ammeter is connected to the auxiliary electrode disposed within the sleeve of the semiconductor material. The other end of the ammeter is generally connected to either end of the coil.

There are two ways of measuring the current flow in the semiconductor. The first is to connect the south pole of the coil to the negative terminal of the ammeter and the auxiliary electrode to the positive terminal of the ammeter. The second method of measurement is to connect the north pole of the coil to the positive terminal of the ammeter and the auxiliary electrode to the negative terminal of the ammeter.

In the absence of any specific gas to be measured, the electrical current induced by the magnetic field is small due to the limited number of free electrons in the semiconductor. However, when a specific gas, such as a hydrocarbon, is in contact with the semiconductor, the number of electrons in the semiconductor is increased due to the number of electrons being transferred from the gaseous molecules to the semiconductor by means of chemisorption. The number of electrons transferred from the gas to the semiconductor is dependent on the concentration of the specific gas. The increased number of electrons thus causes a higher current flow. This increase in the electrical current induced by the electromagnetic field provides a measure of the concentration of a specific gas.

It is an object of the present invention to provide a gas detector which uses an active semiconductor as a sensing element for detecting a variety of different gases.

Other objects and features of the present invention will become apparent from the following detailed description considered in connection with the accompanying drawing which discloses the embodiments of the invention. It is to be understood, however, that the drawing is designed for the purpose of illustration only and not as a definition of the limits of the invention.

In the drawing wherein similar reference characters denote similar elements throughout the several views.

Figure 3:
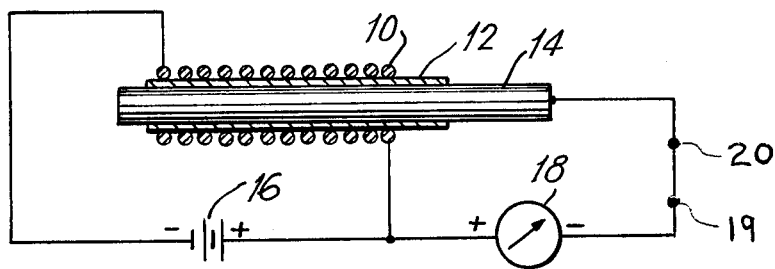

FIG. 3 discloses another electrical connection for measuring the concentration of the gas.

Figure 1:
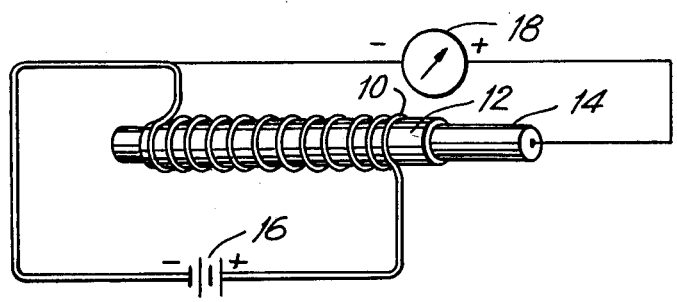
FIG. 1 is a perspective view partly in schematic form showing the use of the present invention in a measuring circuit.
Figure 2:
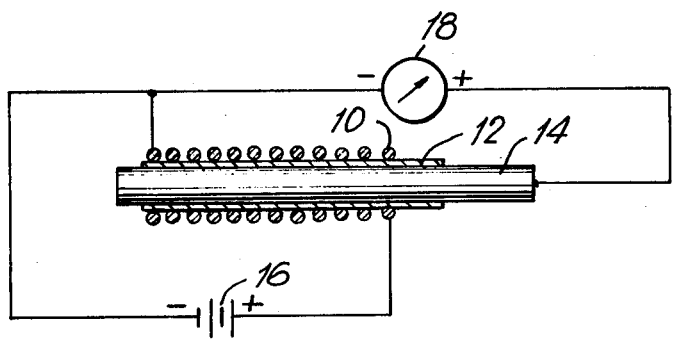
FIG. 2 is a cross-sectional view of the sensing element of FIG. 1.

In FIGS. 1 and 2, there is shown a coil 10 which is helically wrapped around a sensing element 12 constructed in the form of an elongated sleeve. Disposed within that sleeve and having a diameter slightly smaller than the internal diameter of the coil is an auxiliary electrode preferably constructed of a solid wire. One end of the wire is connected to the positive terminal of an ammeter 18. The negative terminal of the ammeter is connected to the negative terminal of a battery or DC supply 16 which is shown connected across the terminal of coil 10. Ammeter 18 is designed to measure the electron flow between coil 10 through sensing material 12 to electrode 14.

Coil 10 is preferably constructed of a noble metal, such as platinum, so that it is capable of withstanding high temperatures without oxidizing, or chemically interacting with sensing material 12. Sensing material 12 is preferably a metal oxide either pure or mixed to form a solid state thermal electromagnetic sensor. A number of different metal oxides have been tested and have been found suitable for specific types of gases.

For hydrocarbons detections, zinc oxide, stannic oxide, and gallium oxide are preferable. For the detection of hydrogen, tungsten trioxide or molybdenum trioxide mixed with silicon dioxide are preferred. The sensing material is not restricted to metal oxide of the n-type semiconductor but may also consist of other types of semiconductors.

The auxiliary electrode 14 is constructed of a wire which is preferably chosen from a noble metal family, such as platinum to prevent oxidation and interaction with the semiconductor material.

The sensitivity of the solid state thermal electromagnetic sensors is dependent upon the thickness of the sensing material between the coil and the auxiliary electrode. During operation, either a constant DC voltage or a constant DC current is applied across the coil. This is the only power required by the sensor. The power requirement does vary from one sensor to another. The electrical current induced by the electromagnetic field is measured with the ammeter connected to the auxiliary electrode and one end of the coil. In FIGS. 1 and 2, the meter is shown connected to the negative terminal of the battery or DC supply or to the south pole of the coil. In FIG. 3, the ammeter is shown connected to the north pole of the coil.

The thermal electromagnetic sensor of the present invention has several advantages over the prior art. Namely, it is a solid state device and can be used over a wide temperature range. It is also an active type device and is simpler in operation than passive type gas detectors which require another potential across the sensing material to operate. However, the sensor of the present invention may also consist of a combination of an active and passive device if the conductor is removed between terminals 19 and 20 and a battery substituted so that the negative terminal is connected to terminal 20 and the positive terminal is connected to terminal 19. This improves the sensitivity of the readings detected by ammeter 18. In the basic construction of the present invention, a large number of sensors can be fabricated for various specific gas detections by varying the sensing material and the operating temperature. In comparison with the conventional electrochemical concentration cell gas detector, the solid state thermal electromagnetic sensor of the present invention does not require a reference gas supplied to the reference electrode. This simplifies the operation of the present invention considerably. It may be helpful in the understanding of the invention to refer to the following examples:

In these examples, all thermal electromagnetic sensors were made with the following specifications. A piece of platinum wire with 2 mils diameter and 1¼ inches in length is used for the coil. The coil is made with the center portion of this wire, it has 20 turns with an inner diameter of 8 mils. The space between each turn is 2 mils so the total length of the coil is .78 mils. The electrode is made of a piece of platinum wire with a diameter of 6 mils. The thickness of the sensing material between the coil and the electrode is 1 mil; however, additional sensing material is added between turns of coil to ensure ohmic contact.

EXAMPLE 1

A sensor using gallium oxide as the sensing material is made according to the described specifications. When a constant dc current of 450 mA is passed through the coil, the output of the sensor (the electrode is connected to the positive terminal of the ammeter, and the other terminal of the ammeter is connected to the negative end of the coil) changes from 0.5 uA in air to 4uA in 1% of $CH_4$ (methane) in air (20% of lower explosive limit of methane). When the dc current passing through the coil is raised to 475 mA, the output of the sensor changes from 1.5 uA in air to 29 uA in 1% of $Ch_4$ (methane) in air.

EXAMPLE 2

A sensor using stannic oxide as the sensing material is made with the same specifications. The results are: When a dc current of 375 mA is passed through the coil, the output of the sensor changes from 0.5 uA in air to 2.5 uA in 1% of $Ch_4$(methane) in air. When a current of 400 mA is passed through the coil, the output of the sensor changes from 2 uA in air to 12.5 uA in 1% $CH_4$ (methane) in air. When the dc current passing through the coil is raised to 425 mA, the output of the sensor changes from 9 uA in air to 41 uA in 1% $CH_4$ (methane) in air.

The current output of the sensor can be increased by adding a conductivity current in series with the sensor output, such as by adding a three-volt battery across terminals 19 and 20 of FIG. 3 so that the positive terminal is connected to terminal 20.

EXAMPLE 3

A 3V battery is added in series to the sensor output by connecting it across terminals 19 and 20 of FIG. 3. The output of the sensor with gallium oxide as the sensing material is as follows: When 450 mA of current is passed through the coil, the output of the sensor changes from 2 uA in air to 13 uA in 1% methane in air. When a current of 475 mA is passed through the coil, the output of the sensor changes from 5 uA in air to 95 uA in 1% methane in air.

EXAMPLE 4

A 3V dc battery is added in series as per Example 3. The output of the sensor made with stannic oxide as the sensing material is as follows: When a dc current of 375 mA is passed through the coil, the output of the sensor changes from 3 uA in air to 13 uA in 1% of $CH_4$ (methane) in air. When a dc current of 400 mA is passed through the coil, the output of the sensor changes from 8 uA in air to 48 uA in 1% of $CH_4$ (methane) in air. When a dc current of 425 mA is passed through the coil, the output of the sensor changes from 27 uA in air to 280 uA in 1% of $CH_4$ (methane) in air.

The temperature of the coil in the above examples was 300°–450° C.

While only a few embodiments of the present invention have been shown and described, it will be obvious that many changes and modifications may be made thereunto without departing from the spirit and scope of the invention.

What is claimed is:

1. A gas detector for sensing the presence of a gaseous medium comprising:
   a helical coil for connection to a dc power source for generating an electromagnetic field and radiant heat;
   a thin-walled tubular sleeve constructed of an active sensing material having current carriers responsive to an electromagnetic field and disposed in the magnetic and heating fields of said helical coil, said helical coil surrounding said thin-walled tubular sleeve and in contact therewith, said active sensing material being capable of generating a current in response to the current carriers in the presence of a magnetic field at a predetermined temperature; and
   an electrode disposed in said thin-walled sleeve and in surface contact with said sleeve, so when current sensing element is connected between said electrode and one end of said coil, an electromagnetic current will be produced proportional to the concentration of the gas in contact with the outer surface of the sleeve.

2. The gas detector as recited in claim 1 wherein said tubular sleeve is constructed of an n-type semiconductor material selected from the group consisting of zinc oxide, stannic oxide, and gallium oxide for the detection of a hydrocarbon.

3. The gas detector as recited in claim 2 wherein the operating temperature of the sleeve is between 300°–450° C.

4. The gas detector as recited in claim 1 wherein said tubular sleeve is constructed of tungsten trioxide or molybdenum trioxide mixed with silicon dioxide for the detection of hydrogen.

5. The gas detector as recited in claim 4 wherein the percentage of silicon dioxide varies from 10 to 50% by weight and the remaining is either tungsten trioxide or molybdenum trioxide.

6. The gas detector as recited in claim 5 wherein the operating temperature of the hydrogen sensor is in the range of 100°–300° C.

7. The gas detector as recited in claim 1 wherein said coil is constructed of a noble metal.

8. The gas detector as recited in claim 1 wherein said electrode is constructed of a noble metal.

* * * * *

UNITED STATES PATENT OFFICE
CERTIFICATE OF CORRECTION

Patent No. 4,045,729         Dated August 30, 1977

Inventor(s) Jack C. Loh

It is certified that error appears in the above-identified patent and that said Letters Patent are hereby corrected as shown below:

Column 4, line 16, change "Ch4" to $--CH_4--$; and

Column 4, line 24, change "Ch4" to $--CH_4--$.

Signed and Sealed this

Twentieth Day of December 1977

[SEAL]

Attest:

RUTH C. MASON        LUTRELLE F. PARKER
*Attesting Officer*      *Acting Commissioner of Patents and Trademarks*